US006881756B2

(12) United States Patent
Gendimenico

(10) Patent No.: US 6,881,756 B2
(45) Date of Patent: Apr. 19, 2005

(54) METHOD FOR TREATING SKIN DISORDERS

(75) Inventor: Gerard J. Gendimenico, Hillsborough, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 27 days.

(21) Appl. No.: 10/245,670

(22) Filed: Sep. 17, 2002

(65) Prior Publication Data

US 2003/0104016 A1 Jun. 5, 2003

Related U.S. Application Data

(60) Provisional application No. 60/322,662, filed on Sep. 17, 2001.

(51) Int. Cl.[7] ...................... A61K 31/05; A61K 31/215; A61K 31/216; A61K 31/22; A61K 31/225

(52) U.S. Cl. ...................... 514/732; 514/529; 514/544; 514/546; 514/549; 514/729; 514/817; 514/330; 514/331; 514/350; 514/534; 514/535; 514/536; 514/537; 514/626; 514/692; 514/818; 514/858; 514/865; 514/887; 514/969

(58) Field of Search .............................. 514/732, 529, 514/544, 545, 546, 549, 729, 817, 330, 331, 350, 534, 535, 536, 537, 626, 692, 818, 858, 865, 887, 969

(56) References Cited

U.S. PATENT DOCUMENTS

| 4,898,887 A | 2/1990 | Janusz et al. |
| 6,090,811 A | 7/2000 | Jacobs et al. |
| 6,620,419 B1 | 9/2003 | Lintner |

FOREIGN PATENT DOCUMENTS

| JP | 1311019 | 12/1989 |
| JP | 2700071 | 1/1998 |
| WO | WO 00/15188 A1 | 3/2000 |

OTHER PUBLICATIONS

Webster's New World Dictionary of American English, Third College Edition, Simon & Schuster, Inc., New York, 1988, p. 716.*
Derwent Abstract, accession No. 1999–400116, abstracting JP 11158058 (1999).*
Derwent Abstract, accession No. 1999–400134, abstracting JP 11158078 (1999).*
International Search Report, PCT/US 02/29368 dated Jun. 11, 2003.
Patent Abstracts of Japan, vol. 014, No. 106, Feb. 27, 1990, JP 01 311019 Shiseido Co. Ltd. Dec. 15, 1989.
Haraguchi, H., Ishikawa, H. Kubo, I., Antioxidative Action of Diterpenoids from *Podocarpus nagi*, Planta Medica 63 (1997) pp. 213–215.
Kubo, I., Muroi, H., Himejima, M., Antibacterial Activity of Totarol and its Potentiation, Journal of Natural Products, vol. 55, No. 10, (1992), pp. 1436–1440.
Young, J. Young L., Cutaneous Models of Inflammation for the Evaluation of Topical and Systemic Pharmacological Agents, Pharmacological Methods in the Control of Inflammation, (1989) pp. 215–231.
Wenninger, J., McEwen, G.N., International Cosmetic Ingredient Dictionary and Handbook, Seventh Edition, vol. 2, The Cosmetic, Toiletry, and Fragrance Association, (1997), pp. 1612–1613, 1626, 1653–1662, 1673–1686, 1693–1697.

* cited by examiner

*Primary Examiner*—John Pak
(74) *Attorney, Agent, or Firm*—William E. McGowan

(57) ABSTRACT

The present invention relates to a method for reducing inflammation in the skin and/or treating inflammatory skin disorders, pain, or pruritis by topically applying a composition comprising totarol or a pharmaceutically-acceptable ester thereof.

9 Claims, No Drawings

METHOD FOR TREATING SKIN DISORDERS

This application claims benefit of U.S. Provisional Application No. 60/322,662, filed on Sept. 17, 2001.

FIELD OF THE INVENTION

The present invention relates to a method for treating skin disorders.

BACKGROUND OF THE INVENTION

Totarol belongs to the terpenoid family of natural products. The primary source of totarol is the Podocarp tree (*Podocarpus totara*), native to New Zealand. Totarol can be extracted from the heartwood of decayed Podocarp trees.

Totarol is known to be an antibacterial agent with potent effects on Gram-positive organisms, including *S. mutans, B. subtilis, S. aureus* and *P. acnes*. See Kubo I, et al. J Nat Prod 55:1436–1440 (1992). The topical use of totarol as an antibacterial agent is described in Japanese Patent No. 2,700,071 B2.

Antioxidant effects of totarol have also been described using in vitro systems. These include inhibition of linoleic acid oxidation and suppression of lipid peroxidation in mitochondria and microsomes. See Haraguchi H, et al. Planta Medica 63:213–215 (1997).

Applicants have surprisingly found that totarol is also effective as a topical anti-inflammatory agent.

SUMMARY OF THE INVENTION

In one aspect, the invention features a method for reducing inflammation in the skin by topically applying a composition comprising totarol or a pharmaceutically-acceptable ester thereof.

In another aspect, the invention features a method for treating an inflammatory skin disorder by topically applying a composition comprising totarol or a pharmaceutically-acceptable ester thereof. In one embodiment, the inflammatory skin disorder is an inflammatory skin disorder other than acne.

In another aspect, the invention features a method for treating pain or pruritis by topically applying a composition comprising totarol or a pharmaceutically acceptable ester thereof.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, all percentages of ingredients are percentages by weight (% W/W).

Definitions

As used herein, "topical application" or "topically applying" means directly laying on or spreading on outer skin using, e.g., by use of the hands or an applicator such as a wipe.

As used herein, "pharmaceutically-acceptable" means that totarol or ester thereof, pharmaceutically active agents or inert ingredients which the term describes are suitable for use in contact with tissues (e.g., the skin) without undue toxicity, incompatibility, instability, irritation, allergic response, and the like, commensurate with a reasonable benefit/risk ratio.

As used herein, "safe and effective amount" means an amount of compound or composition (e.g., the totarol or a pharmaceutically acceptable ester thereof) sufficient to significantly induce a positive modification in the condition to be regulated or treated, but low enough to avoid serious side effects. The safe and effective amount of the compound or composition will vary with the age and physical condition of the end user, the severity of the condition being treated/prevented, the duration of the treatment, the nature of concurrent therapy, the specific compound or composition employed, the particular pharmaceutically-acceptable topical carrier utilized, and like factors.

Totarol

The composition utilized in the present invention comprises totarol or a pharmaceutically-acceptable ester thereof. Totarol is a compound having the structure shown below in FIG. 1.

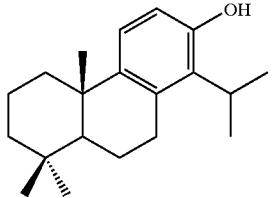

FIG. 1

In one embodiment, the composition comprises a safe and effective amount of totarol or a pharmaceutically acceptable ester thereof. In one embodiment, the composition comprises a safe and effective amount of totarol. In one embodiment, totarol is isolated from a natural source. Examples of such natural sources include, but are not limited to, the Podocarp tree and plants from the Cupressacaeae family. In one embodiment, totarol is synthetically manufactured. In one embodiment, the totarol or a pharmaceutically acceptable ester thereof is present in the composition in an amount from about 0.01% to about 20% by weight of the total composition, in particular in an amount from about 0.1% to about 5% by weight of the total composition.

Pharmaceutically-Acceptable Salts or Esters

Examples of pharmaceutically acceptable salts include, but are not limited to, those with pharmaceutically acceptable organic acids (e.g., acetic, lactic, maleic, citric, malic, ascorbic, succinic, benzoic, methesulfonic, toluenesulfonic, or pamoic acid), as well as polymeric acids (e.g., tannic or carboxymethyl cellulose) and salts with inorganic acids such as a hydrohalic acid (e.g., hydrochloric acid, sulfuric acid, or phosphoric acid). Examples of pharmaceutically acceptable esters include, but are not limited to, C2–C6 alkyl esters such as methyl esters and ethyl esters.

Topical Compositions

The topical compositions useful in the present invention involve formulations suitable for topical application to skin. In one embodiment, the composition comprises the totarol or a pharmaceutically-acceptable ester thereof and a pharmaceutically-acceptable topical carrier. In one embodiment, the pharmaceutically-acceptable topical carrier is from about 50% to about 99.99%, by weight, of the composition (e.g., from about 80% to about 95%, by weight, of the composition.

The compositions may be made into a wide variety of product types that include but are not limited to lotions, creams, gels, sticks, sprays, shaving creams, ointments, cleansing liquid washes and solid bars, shampoos, pastes, powders, mousses, shaving creams, wipes, patches, nail lacquers, wound dressing, adhesive bandages, hydrogels, films and make-up such as concealers, foundations, mascaras, and lipsticks. These product types may comprise several types of pharmaceutically-acceptable topical carriers including, but not limited to solutions, emulsions (e.g., microemulsions and nanoemulsions), gels, solids, micelles, and liposomes. The following are non-limitative examples of such topical carriers. Other topical carriers can be formulated by those of ordinary skill in the art.

The topical compositions useful in the present invention can be formulated as solutions. Solutions typically include an aqueous solvent (e.g., from about 50% to about 99.99%, such as from about 90% to about 99%, by weight of a pharmaceutically acceptable aqueous solvent).

Topical compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. See the International Cosmetic Ingredient Dictionary and Handbook, eds. Wenninger and McEwen, pp. 1656–61, 1626, and 1654–55 (The Cosmetic, Toiletry, and Fragrance Assoc., Washington, D.C., 7$^{th}$ Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in the ICI Handbook pp. 1693–1697.

The topical compositions useful in the present invention can also be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in the ICI Handbook, pp.1673–1686.

Lotions and creams can be formulated as emulsions. Typically, such lotions comprise from about 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type are also useful in the subject invention. In general, such single or multiphase emulsions contain water, emollients, and emulsifiers as essential ingredients.

The topical compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical compositions of the present invention can also be formulated into a solid formulation (e.g., a wax-based stick, soap bar composition, powder, or a wipe containing powder).

Liposomal formulations are also useful compositions of the subject invention. Examples of liposomes are unilamellar, multilamellar, and paucilamellar liposomes, which may or may not contain phospholipids. Liposomes typically have size from about 50 nm to about 10 microns, such as about 0.1 to about 1 microns. Such compositions can be prepared by first combining hesperetin with a phospholipid, such as dipalmitoylphosphatidyl choline, cholesterol and water. Epidermal lipids of suitable composition for forming liposomes may be substituted for the phospholipid. Example of such epidermal lipids include, but are not limited to, glyceryl monoesters and diesters, polyethylene fatty ethers, and sterols. The liposome preparation may then incorporated into one of the above carriers (e.g., suspended in a solution, gel, or an oil-in-water emulsion) in order to produce the liposomal formulation.

Micelle formulations are also useful compositions of the subject invention. Such compositions can be prepared using single chain surfactants and lipids. Micelles typically have size from about 1 nm to about 100 nm, such as from about 10 nm to about 50 nm. The micelle preparation may then incorporated into one of the above carriers (e.g., a gel or a solution) in order to produce the micelle formulation.

The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Pharmaceutically Active Agents

In one embodiment, the topical composition further comprises another pharmaceutically active agent in addition to the totarol or a pharmaceutically acceptable ester thereof. What is meant by a "pharmaceutically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, spin traps, retinoids such as retinoic acid, retinol and retinyl palmitate, ceramides, polyunsaturated fatty acids, essential fatty acids, enzymes such as proteases (e.g., trypsin), enzyme inhibitors, minerals, hormones such as estrogens, steroids such as hydrocortisone, 2-dimethylaminoethanol, copper salts such as copper chloride, coenzyme Q10, peptides such as those disclosed in PCT Patent Application WO00/15188, lipoic acid, amino acids such as proline and tyrosine, vitamins, lactobionic acid, acetyl-coenzyme A, niacin, riboflavin, thiamin, ribose, electron transporters such as NADH and FADH2, and other botanical extracts such as aloe vera and soy, and derivatives and mixtures thereof. The pharmaceutically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited, to glycolic acid, lactic acid, malic acid, salicylic acid, citric acid, and tartaric acid.

In one embodiment, the composition further comprises another anti-inflammatory agent. In one embodiment, the composition comprises a safe and effective amount of an anti-inflammatory agent selected from the group consisting of corticosteroids such as hydrocortisone, betamethasone, mometasone, alclometasone, clobetasol, prednicarbate, and pharmaceutically-acceptable salts and esters thereof, non-steroidal anti-inflammatory agents such as COX inhibitors, LOX inhibitors, and p38 kinase inhibitors, immunosuppresant agents such as cyclosporin, and cytokine synthesis inhibitors.

In one embodiment, the composition further comprises an analgesic and/or anti-pruritis agent. In one embodiment, the composition comprises a safe and effective amount of menthol, camphor, an antihistamine, a local anesthetic such as tetracaine, lidocaine, prilocaine, benzocaine, bupivacaine, mepivacaine, dibucaine, etidocaine, butacaine, cyclomethycaine, hexylcaine, proparacaine, and lopivacaine, capsaicin, and oatmeal.

The anti-inflammatory, analgesic, or anti-pruritis agent typically will be present in the composition in an amount from about 0.001% to about 10% by weight, in particular in an amount from about 0.01% to about 2% by weight.

In one embodiment, the composition contains an antioxidant. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopheryl acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612–13 of the ICI Handbook.

Other Materials

Various other materials may also be present in the compositions useful in the subject invention. These include humectants, preservatives, chelating agents, and pH adjusters. Examples of such agents are disclosed in the ICI Handbook, pp. 1661–62, 1654–55, 1626, and 1653, respectively. In addition, the topical compositions useful herein can contain conventional cosmetic adjuvants, such as dyes, pigments, and fragrances.

Mineral Water

The compositions of the present invention may be prepared using a mineral water. In one embodiment, the mineral water has a mineralization (i.e., the sum of the concentrations of anions and cations present in the water) of at least about 200 mg/L (e.g., from about 300 mg/L to about 1000 mg/L). In one embodiment, the mineral water comprises at least about 10 mg/L of calcium and/or at least about 5 mg/L of magnesium.

Topical Application

In one embodiment, the composition is topically applied at least once a week, such as once or twice a day. In one embodiment, the composition is topically applied until the inflammation, inflammatory skin disorder, pain, and/or pruritis has been reduced or eliminated to the satisfaction of the user (e.g., a human).

Examples of inflammatory skin disorders include, but are not limited to, acne, eczema, psoriasis, infections, dermatitis such as contact dermatitis, atopic dermatitis, seborrheic dermatitis, and allergic dermatitis, polymorphous light eruptions, folliculitis, alopecia, poison ivy, insect bites, acne inflammation, and irritation induced by extrinsic factors such as chemicals, trauma, pollutants (such as cigarette smoke), and sun exposure.

EXAMPLE 1

Allergic contact dermatitis is an animal model of skin inflammation that mimics many aspects of human skin inflammation. See Young J M, De Young L M, Cutaneous Models of Inflammation for the Evaluation of Topical and Systemic Pharmacological Agents; In: *Pharmacological Methods in the Control of Inflammation*, Alan R. Liss, Inc, pp. 215–231 (1989). This model was used to demonstrate the anti-inflammatory activity of totarol. The inflammatory response is established by using oxazolone as the chemical sensitizer. A topical anti-inflammatory agent is assessed by measuring its ability to suppress the ear swelling reaction after applying a challenge dose of oxazolone to the ear followed by the test agent.

In this assay, the totarol (Mende-DEK Limited, Masterton, New Zealand) was evaluated against hydrocortisone, a steroid known to inhibit allergic contact dermatitis. Albino male CD-1 mice, 7–9 weeks old, were induced on the shaved abdomen with 50 $\mu$L of 3% oxazolone in acetone/corn oil (Day 0). On Day 5, a 20 $\mu$L volume of 2% oxazolone in acetone was applied to the dorsal left ear of the mouse. Test agents were applied to the left ear (20 $\mu$L) 1 hour after oxazolone challenge in a 70% ethanol/30% propylene glycol vehicle. The right ear was not treated. The mice were sacrificed by $CO_2$ inhalation 24 hours after the oxazolone challenge, the left and right ears were removed and a 7-mm biopsy was taken from each ear and weighed. The difference in biopsy weights between the right and left ear was calculated and is set forth in Table 1. Anti-inflammatory effects of compounds are evident as an inhibition of the increase in ear weight.

TABLE 1

| Treatment | Dose, as % w/v | % Inhibition of the Ear Swelling Response* |
|---|---|---|
| Hydrocortisone | 0.1 | 84.2 |
|  | 0.01 | 65.5 |
|  | 0.001 | 36.0 |
| Totarol | 1 | 82.3 |
|  | 0.3 | 80.0 |
|  | 0.03 | 44.6 |

*% Inhibition = ((Vehicle Biopsy Weight − Treatment Biopsy Weight)/ Vehicle Biopsy Weight) × 100

Totarol was highly effective as a topical anti-inflammatory agent with dose-dependent inhibition of the inflammatory response. At its two highest doses, totarol was equivalent in activity to the highest dose of hydrocortisone.

EXAMPLE 2

Neurosensory inflammation, also referred to as neurogenic inflammation, is a type of inflammation triggered by sensory nerve activation in skin. Certain natural substances that act on vanilloid receptors cause the nerves (C-fibers) to release inflammatory neuropeptides such as substance P and calcitonin gene-related peptide. In mouse skin, an edema response rapidly occurs upon application of either the vanilloid receptor activators, capsaicin or resiniferatoxin. Compounds that inhibit the response to neurosensory stimulation could be useful as topical analgesics, itch inhibitors or soothing agents for irritated or damaged skin. See U.S. Pat. No. 6,090,811.

Albino male CD-1 mice, 7–9 weeks old, were used. Resiniferatoxin alone (0.05%) or a combination of 0.05% resiniferatoxin with test compound was made in acetone. A 20-μl volume of the solutions was applied to the left ears (10 mice per treatment group). The right ear was not treated. The mice were sacrificed by $CO_2$ inhalation 30 minutes after applying the solutions. The left and right ears were removed and a 7-mm biopsy was removed from each ear and weighed. The difference in biopsy weights between the right and left ear was calculated. The percent inhibition was calculated by comparing treatments to resiniferatoxin alone. Anti-edema effects of compounds are evident as an inhibition of the increase in ear weight. These results are set-forth in Table 2.

TABLE 2

| Treatment | Topical Dose, as % w/v | % Inhibition of the Ear Edema* |
|---|---|---|
| Arvanil | 0.5 | 26.8 |
| Totarol | 1 | 46.6 |

*% Inhibition = ((Vehicle Biopsy Weight − Treatment Biopsy Weight)/ Vehicle Biopsy Weight) × 100

Totarol was highly effective in this model. As a comparison, arvanil a known analgesic compound and an analog of capsaicin (described in U.S. Pat. No. 4,898,887), was also active.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method for treating pain or pruritis, said method comprising topically applying to a subject in need of treatment for pain or pruritis a composition comprising totarol or a pharmaceutically-acceptable ester thereof, wherein said totarol or a pharmaceutically-acceptable ester thereof was isolated from a natural source or synthetically made.

2. A method of claim 1, wherein said method is for treating pain.

3. A method of claim 1, wherein said method is for treating pruritis.

4. A method of claim 2, wherein said composition comprises totarol.

5. A method of claim 3, wherein said composition comprises totarol.

6. A method of claim 2, wherein said composition further comprises tetracaine, lidocaine, prilocaine, benzocaine, bupivacaine, mepivacaine, dibucaine, etidocaine, butacaine, cyclomethycaine, hexylcaine, proparacaine, or ropivacaine.

7. A method of claim 3, wherein said composition further comprises menthol or camphor.

8. A method of claim 4, wherein said totarol or a pharmaceutically-acceptable ester thereof was synthetically made.

9. A method of claim 5, wherein said totarol or a pharmaceutically-acceptable ester thereof was synthetically made.

* * * * *